United States Patent [19]
Spievack et al.

[11] Patent Number: 5,591,170
[45] Date of Patent: Jan. 7, 1997

[54] INTRAMEDULLARY BONE CUTTING SAW

[75] Inventors: Alan R. Spievack, Cambridge; Fernando A. de Toledo, Concord, both of Mass.

[73] Assignee: Genesis Orthopedics, Cambridge, Mass.

[21] Appl. No.: 324,514

[22] Filed: Oct. 14, 1994

[51] Int. Cl.$^6$ .................. A61B 17/14; A61B 17/16
[52] U.S. Cl. .............. 606/82; 30/166.3; 30/122; 606/80; 606/177; 606/178
[58] Field of Search ................. 606/170, 171, 606/172, 173, 174, 175, 176, 177, 178, 179, 180, 79, 80, 82, 83, 84, 85; 408/180, 187, 188; 30/393, 166.3, 122

[56] References Cited

U.S. PATENT DOCUMENTS

| | | | |
|---|---|---|---|
| 2,702,550 | 2/1955 | Rowe . | |
| 3,412,733 | 11/1968 | Ross . | |
| 3,468,312 | 9/1969 | Kuntscher | 606/176 |
| 4,543,718 | 10/1985 | Duescher | 30/166.3 |
| 4,895,146 | 1/1990 | Draenert | 606/79 |
| 4,936,313 | 6/1990 | Burkhardt et al. . | |
| 4,966,604 | 10/1990 | Reiss | 606/159 |
| 5,122,134 | 6/1992 | Borzone et al. | 606/80 |
| 5,152,772 | 10/1992 | Sewell, Jr. | 606/170 |
| 5,178,625 | 1/1993 | Groshong | 606/159 |
| 5,192,291 | 3/1993 | Pannek, Jr. | 606/159 |
| 5,201,749 | 4/1993 | Sasche et al. | 606/171 |
| 5,217,474 | 6/1993 | Zacca et al. | 606/159 |
| 5,224,945 | 7/1993 | Pannek, Jr. | 606/159 |

OTHER PUBLICATIONS

Brochure on an endomedullary saw, consisting of pp. 6, 8 and 11.

*Primary Examiner*—Michael Powell Buiz
*Assistant Examiner*—Scott B. Markow
*Attorney, Agent, or Firm*—Hamilton, Brook, Smith & Reynolds, P.C.

[57] ABSTRACT

A powered bone cutting saw is used from within the intramedullary canal of a bone. A cutting blade is inserted through a bored intramedullary canal to a predetermined cutting depth. A motor is coupled to the cutting blade to rotate the cutting blade. The blade is extended to a cutting position and operated by a surgeon to cut the bone radially from the inside outwardly, transversely, to the intramedullary canal. Gearing selectable by the surgeon permits the blade to oscillate. The motor can also be coupled to a reamer tip for boring the intramedullary canal. The apparatus, including the reamer tip, can be cannulated to accept a guide wire.

67 Claims, 8 Drawing Sheets

INTRAMEDULLARY BONE CUTTING SAW

BACKGROUND OF THE INVENTION

During orthopedic surgery, it may be necessary to separate a bone into sections. For example, bone lengthening surgery requires that a bone be cut through to create a proximal and a distal section. Similarly, in bone shortening surgery, the bone is cut through in two places and a middle section of bone is removed. To avoid unnecessary laceration of skin and tissue surrounding the bone, various tools have been developed to cut the bone from within the intramedullary canal.

Existing intramedullary bone saws are hand operated by a surgeon. The surgeon turns a drive shaft by hand to rotate cutting blades against the bone. It can take about thirty minutes for the surgeon to cut through a human femur by hand. In addition to these time requirements placed on the surgical team and the patient, the act of manually cutting the bone can be physically tiring to the surgeon.

SUMMARY OF THE INVENTION

Briefly, a powered bone cutting saw having an extendable cutting blade is employed according to the invention to solve the above deficiencies of the prior art. The cutting blade is inserted through a bored intramedullary canal to a predetermined cutting depth. A motor is coupled to the cutting blade to operate the cutting blade. The blade is then extended to a cutting position and operated to cut the bone radially from the inside outwardly, transversely to the longitudinal axis of the bone.

Preferably, the saw comprises an elongate tubular member, a cutting blade, an elongate actuating member, an activator and a motor. The elongate tubular member is inserted longitudinally into the bored intramedullary canal of a bone to a predetermined cutting depth. The cutting blade is extendable from a rest position having a cutting diameter less than the diameter of the bored intramedullary canal to a working position having a cutting diameter greater than the diameter of the intramedullary canal. The elongate actuating member is disposed within the tubular member and coupled to the cutting blade, such that displacement of the actuating member radially extends the cutting blade from the rest position to the working position. The activator is used to displace the actuating member in response to actions of a surgeon. The saw can be integrated with a reamer to form a surgical tool, which preferably has a cannulation along the length for receiving a guide wire.

The motor operates to actuate the tubular member such that the extended cutting blade is operated in response to the operation of the tubular member. The cutting blade can be operated in a rotation mode or an oscillation mode, as selected by the surgeon. In the oscillation mode, the cutting blade cuts bone tissue but not soft tissue surrounding the bone. This rotation or oscillation of the cutting blade causes the bone to be cut radially from the inside out and transverse to the intramedullary canal.

The above and other features of the invention, including various novel details of construction and combination of parts, will now be more particularly described with reference to the accompanying drawings and pointed out in the claims. It will be understood that the particular intramedullary bone cutting saws embodying the invention are shown by illustration only and not as a limitation of the invention. The principle and features of this invention may be employed in varied and numerous embodiments without departing from the scope of the invention.

DETAILED DESCRIPTION OF PREFERRED EMBODIMENTS OF THE INVENTION

Figures 1, 2:
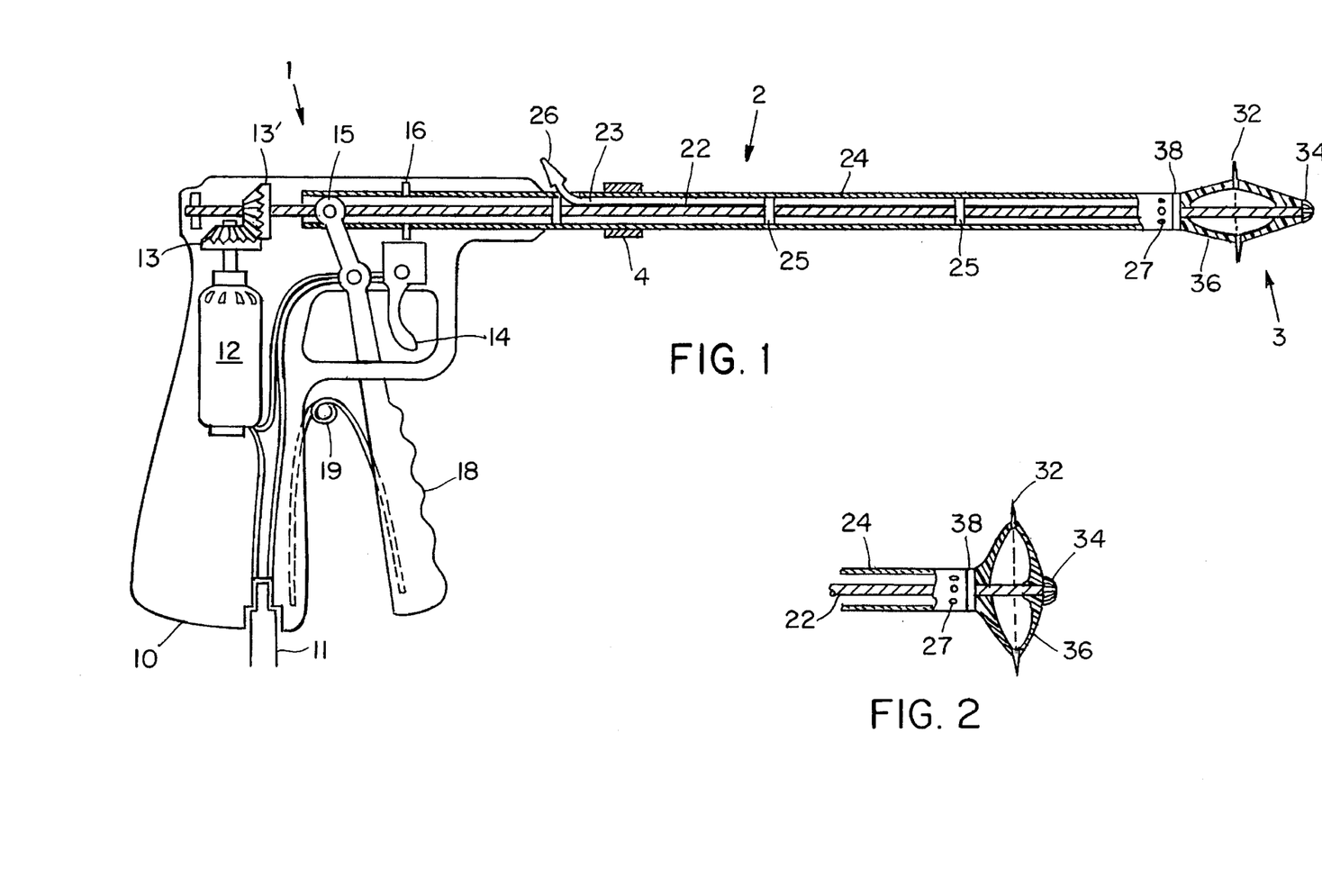
FIG. 1 is a schematic diagram partially in section of a preferred bone saw according to the invention.
FIG. 2 is a schematic diagram of an extended cutting blade of the bone saw of FIG. 1.

FIG. 1 is a schematic diagram partially in section of a bone saw according to the invention. The bone saw comprises a drive body 1, a shaft 2 and a surgical head 3. During use, the shaft 2 and surgical head 3 are inserted into a bored intramedullary canal of a bone as will be seen in FIG. 7. A depth stop 4 clamps over the shaft 2 at a predetermined distance from a cutting blade 32 on the surgical head 3. The shaft 2 can be either a rigid member for use with a particular bone, such as a bone having relatively straight canals, or a flexible member for use with different bones, such a bones having relatively curved canals and canals having an awkward surgical approach (e.g., the tibia).

The body 1 comprises a housing 10, an activation handle 18 and a speed control trigger 14. The activation handle 18 is coupled to the housing 10 by a spring mechanism 19, which is biased to place the activation handle 18 in a steady state position (i.e., opened).

The shaft 2 includes an internal drive shaft 22 and an outer tube 24. The drive shaft 22 is suspended within the outer tube 24 by shaft bearings 25 spaced along the length of the outer tube 24. A saline irrigation nozzle 26 supplies irrigating saline solution into the outer tube 24 through an irrigation conduit 23. The saline exits from the outer tube 24 through an irrigation hole or holes 27 at the distal end. The saline rinses and cools the bone during cutting.

A variable speed motor 12 within the drive body 1 is coupled to a power source (not shown) by a coupling 11. The motor 12 rotates a first bevel gear 13, which meshes with and rotates a second bevel gear 23. The drive shaft 22 is coupled to the second bevel gear 23 and is thus rotated by the motor 12. The speed control trigger 14 is electrically coupled to the motor 12 so that a surgeon can vary the speed of rotation of the drive shaft 22. Preferably, the drive shaft 22 is rotated at a speed of about 110 revolutions per minute (rpm) or less. If rotated too fast, the blade may jam or burn the bone tissue. If bone cells are killed, then the cut bone may not heal properly.

The surgical head 3 is positioned at the distal end of the drive shaft 22, which is secured to the surgical head 3 by a fastening nut 34. The surgical head 3 includes a cutting blade 32. In the particular embodiment of FIG. 1, the surgical head 3 includes an elastomer body 36, to which the cutting blade 32 is secured. The elastomer body 36 is preferably bulbous and the cutting blade 32 includes a plurality of teeth spaced around the central circumference of the elastomer body 36. As illustrated in FIG. 1, the cutting blade 32 is positioned in a rest position, where the tip-to-tip diameter of the cutting blade 32 is less than the diameter of the bored intramedullary canal.

For cutting, the cutting blade 32 is extended from the FIG. 1 rest position to a cutting position. FIG. 2 is a schematic diagram of the cutting blade 32 of the bone saw of FIG. 1 in the extended or cutting position. By squeezing the activation handle 18, the surgeon drives the outer tube 24 forward due to a coupling 15 between the outer tube 24 and the activation handle 18. As the outer tube 24 is urged forward, the distal end of the outer tube 24 is placed in contact with a thrust bearing 38 of the cutting head 3. The thrust bearing 38 is thus urged toward the distal end of the drive shaft 22, and compresses the elastomer body 36 to create a bulge at the central circumference of the elastomer body 36, which radially extends the cutting blade 32.

The cutting diameter of the cutting blade 32 is determined by the linear movement of the outer tube 24. As the surgeon continues to squeeze the activation handle 18, the cutting diameter of the cutting blades 32 increases. A guide pin 16 registered to a guide channel 160 (FIG. 3) limits the forward motion of the outer tube 24, which limits the cutting diameter of the cutting blade 32. The guide pin 16 can also serve as an indicator of the cutting diameter of the cutting blade 32. When the surgeon releases the activation handle 18, it is returned to its steady state rest position (FIG. 17) by the spring mechanism 19, which results in the return of the cutting blade 32 to its rest (i.e., retracted) position.

Figure 3:
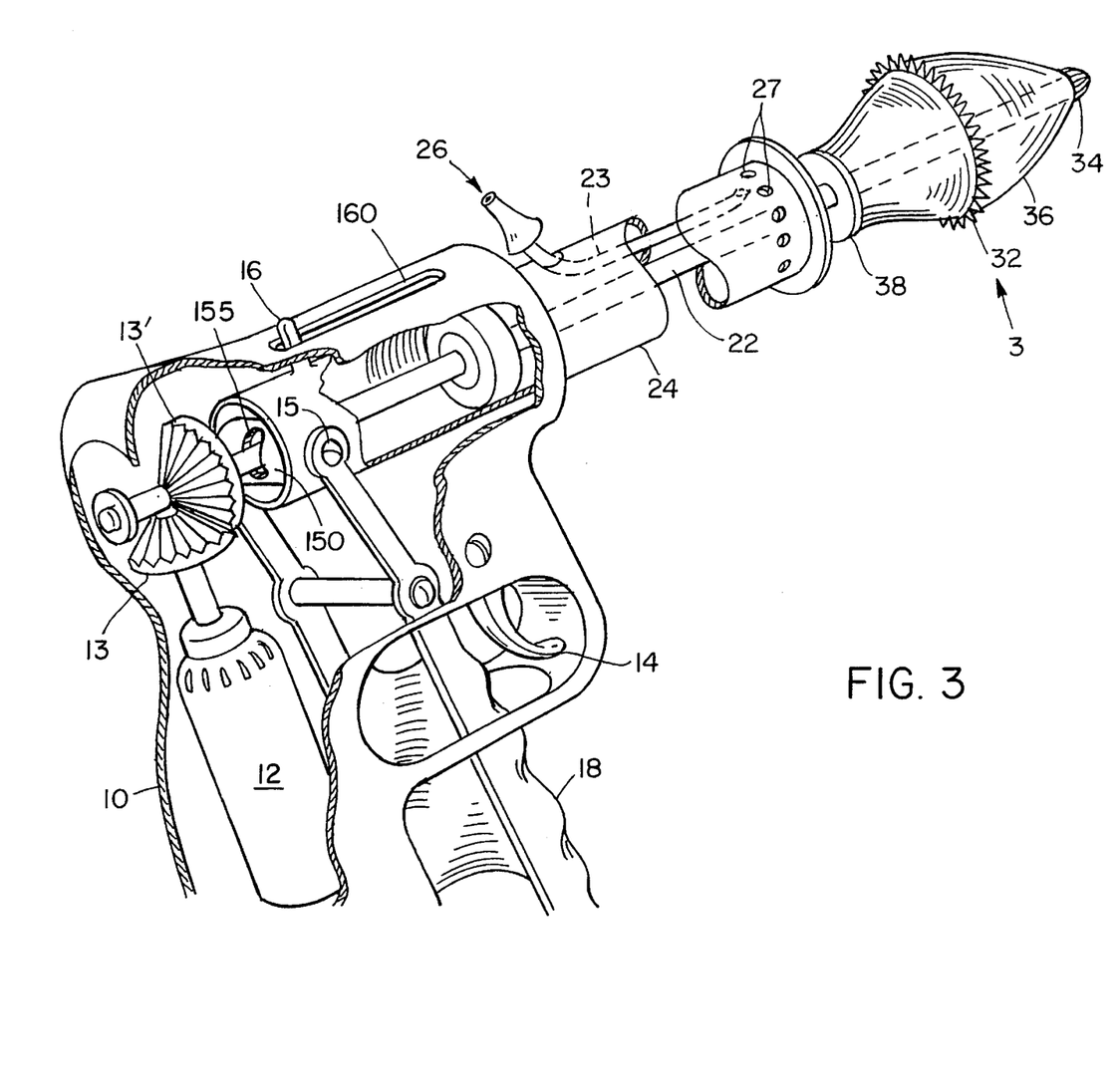
FIG. 3 is a foreshortened perspective view of the bone saw of FIG. 1 with portions of the housing broken away.

FIG. 3 is a foreshortened perspective view of the bone saw of FIG. 1 with portions of the housing 10 broken away. Shown is a spacer 150 extending transversely of the tube 24 and coupled to the drive handle coupling 15. The drive shaft 22 extends through an opening 155 in the spacer 150. Also shown is a guide pin channel 160 which limits movement of the tube 24 by limiting the fore and aft motion of the guide pin 16.

Figure 4:
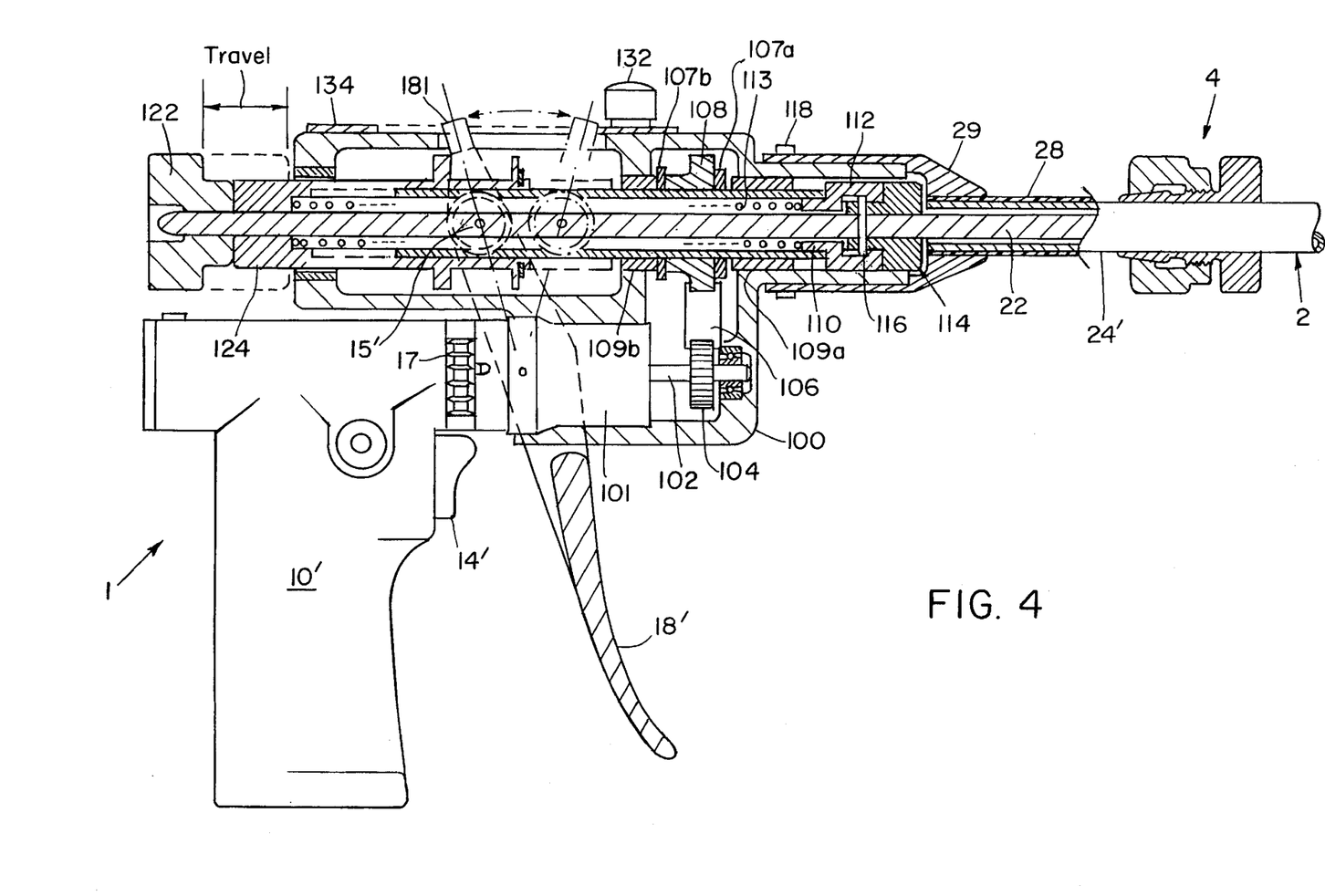
FIG. 4 is a detailed cross sectional diagram of another embodiment of a bone saw according to the invention.

FIG. 4 is a detailed cross sectional diagram of another embodiment of a bone saw according to the invention. Power is provided by a drive unit 10' having an integrated speed control trigger 14'. Preferably, the drive 10' is a commercially available Maxidrive II air drive unit manufactured by 3M Corporation. Other suitable hydraulic, electric or air drive units can be substituted in various embodiments of the invention. The drive unit 10' is coupled to a drive housing 100 by a chuck coupling 101, which can employ a bayonet-type engagement. A spring-loaded thumb screw 17 provides for quick disconnection of the drive unit 10' from the drive housing 100. Alternatively, a motor can be integrated within the drive housing 100.

The shaft 2 comprises a solid drive shaft 22, a stainless steel torque tube 24' and a plastic outer sheath 28. A retaining nut 122 at the rear or proximal end of the housing 100 secures the shaft 2 to the body 1. When the retaining nut 122 is removed, a subassembly including the drive shaft 22, torque tube 24' a distal dog coupling 114 and the cross pin 116 can be extracted from the drive body by pulling the subassembly from the distal end of the drive tube 110.

The drive shaft 22 is urged forward by an activation handle 18' coupled to an activation housing 124 by joint 15'. The range of motion of the activation handle 18' is limited by a stop gate 134. Before inserting the cutting blade 32 into the bone, the surgeon determines the diameter of the bone, depresses the activation handle 18 until the blade 32 is extended to the diameter of the bone, and aligns the stop gate 134 with the tip 181 of the activation handle. The stop gate is then locked in place by a first set screw 132. When the tip 181 of the activation handle 18' contacts the stop gate 134 during use, the cutting blade (not shown) is extended to the maximum radius (or diameter) set by the surgeon. Alternatively, an eccentric or a cam mechanism can be used instead of the stop gate 134.

The bone saw operates as follows. The drive unit 10' rotates a primary drive shaft 102, which is fastened to a first gear 104. The first gear 104 is coupled to a second gear 108 by an idler gear 106. The second gear 108 meshes with a tubular supporting member 110, which is in turn fastened to a proximal dog coupling 112. The distal dog coupling 114 is fastened to the torque tube 24'. The cross pin 116 extends between the drive shaft 22 and the torque tube 24'. With the dog couplings 112,114 mated, the drive shaft 22 and the torque tube 24' rotate under the control of the speed control trigger 14'. Alternatively, a slip clutch can be used in place of the dog couplings 112,114. When the activation handle 18' is released, a spring 113 disposed between the activation housing 124 and the proximal dog coupling 112 expands to automatically displace the activation housing 124 from the proximal dog coupling 112. As the activation housing 124 urges away from the proximal dog coupling 112, the drive shaft 22 is pulled toward the proximal end of the drive housing 100. The cutting blade 32 of the cutting head 3 (FIG. 1) is thus retracted toward the rest position.

The rotating elements are separated from the drive housing 100 by a set of bearings 109a, 109b, 109c. The second gear 108 is spaced apart from a distal bearing 109a by a first thrust washer 107a and from a central bearing 109b by a second thrust washer 107b. The distal and central bearings isolate the supporting member 110 from the drive housing 100. A proximal bearing 109c isolates the activation housing 124 from the drive housing 100.

Figures 5, 6:
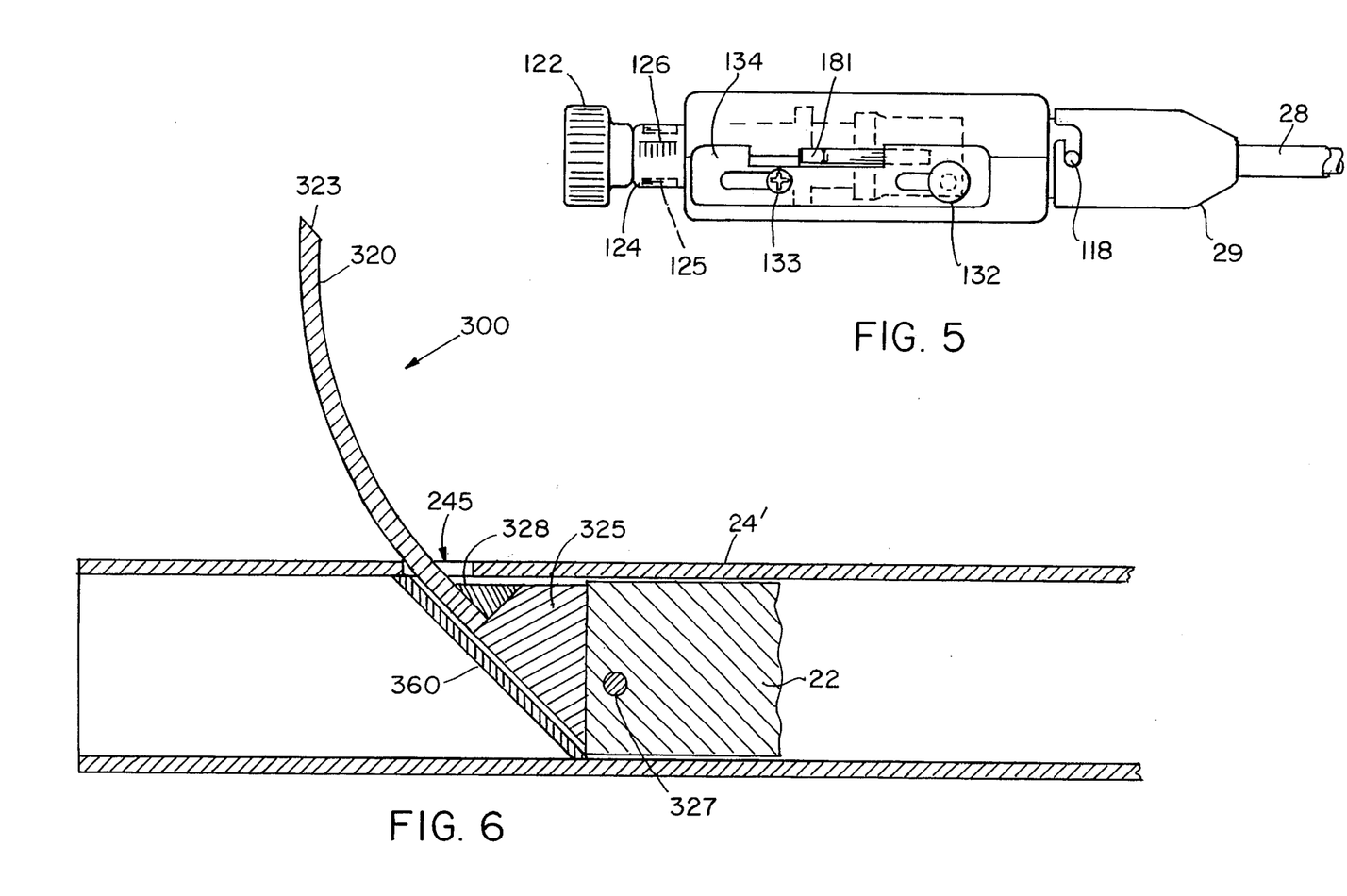
FIG. 5 is a top view of the bone saw of FIG. 4.
FIG. 6 is a cross sectional diagram of a cutting assembly of FIG. 4 with a pivoted cutting blade.

Also shown in FIG. 4 is a nose cap 29 for a flexible polymetric outer tube 28. The nose cap 29 and flexible outer tube 28 are retained in position by bay lock 118 (FIG. 5). After use, the nose cap 29 and outer tube 28 can be cleaned and later reused. Normally, the drive shaft 22, torque tube 24' and surgical head 3 are discarded after use.

FIG. 5 is a top view of the bone saw of FIG. 4. Shown in more detail is the projection stop gate 134 and first set screw 132. Also shown is a second set screw 133, which is used to more firmly secure the position of the stop gate 134. The set screws are clamped by the surgeon to limit fore and aft movement of the blade. Additionally, the activation housing 124 can be calibrated to accurately measure the cutting radius (or diameter). As such, there can be reference marks 126 on the activation housing 124 which indicate the current cutting radius (or diameter) of the cutting blade 32 to the surgeon. Indeed, the reference marks 126 can be used as a guide for setting the position of the stop gate 134.

FIG. 6 is a cross sectional diagram of a cutting assembly 300 with a pivoted cutting blade. Illustrated are the drive shaft 22 and torque tube 24'. The cutting blade 320 is a rigid arc-shaped metal blade member having a blade edge 323. The torque tube 24' has an opening 245 through which the cutting blade 320 projects while in use. A deflection ramp 360 is fastened within the torque tube 24' to direct the cutting blade 320 radially out of the torque tube 24'. The drive shaft 22 is coupled to a blade footing 325 by a pivot 327. A rib or gusset 328 connects the blade footing 325 to the cutting blade 320 to provide additional structural support at that joint.

As the drive shaft 22 is urged toward the distal end of the torque tube 24', the cutting blade 320 extends further and further out from the torque tube 24'. As illustrated, the cutting blade 320 is fully extended. When in this position, the blade edge 323 has a preferred cutting radius of 24 mm. When the drive shaft 22 is pulled toward the proximal end of the drive housing 100 (i.e., to the right), the cutting blade 320 is pulled into the torque tube 24'. When at rest, the blade edge 323 is fully retracted within the torque tube 24'.

Figure 7:
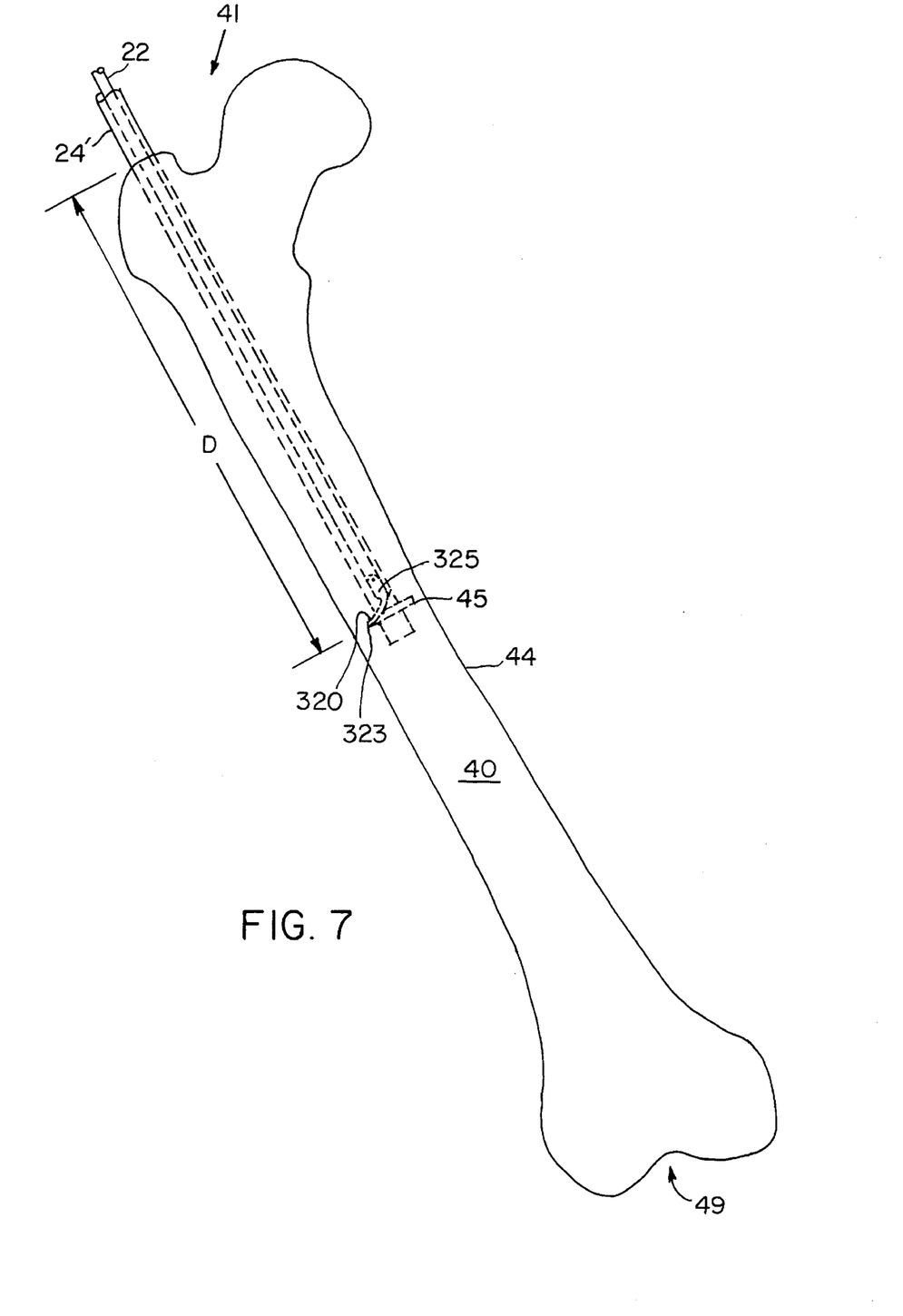
FIG. 7 is a schematic illustration of the bone saw of FIG. 6 cutting a human femur.

FIG. 7 is a schematic illustration of the bone saw of FIG. 6 cutting a human femur 40. The surgeon predetermines the depth D into the bone 40 where the cut is to be made. The depth step 4 is set to the predetermined depth D, as measured from the void 245 in the torque tube 24. The shaft 2 is then inserted into the intramedullary canal through a reamed bore until the depth step 4 contacts the proximal end of the bone 40.

Illustrated in FIG. 7 is the drive shaft 22 and the torque tube 24. For ease of illustration, the sheath 28 is not shown. As illustrated, the blade edge 323 has been extended beyond the torque tube 24 and into the bone 40. The rotation of the shaft 2 cuts a section 45 of the bone 40 progressing radially outward from the drive shaft 22 into the bone 40. The cutting blade 320 is continuously extended until the blade edge 323 extends beyond the outer wall 44 of the bone 40. Alternatively, the blade edge 323 can be stopped by the stop gate 134 or manually by the surgeon just short of the outer wall 44 of the bone 40, at which point the bone is manually fractured.

Figure 8:
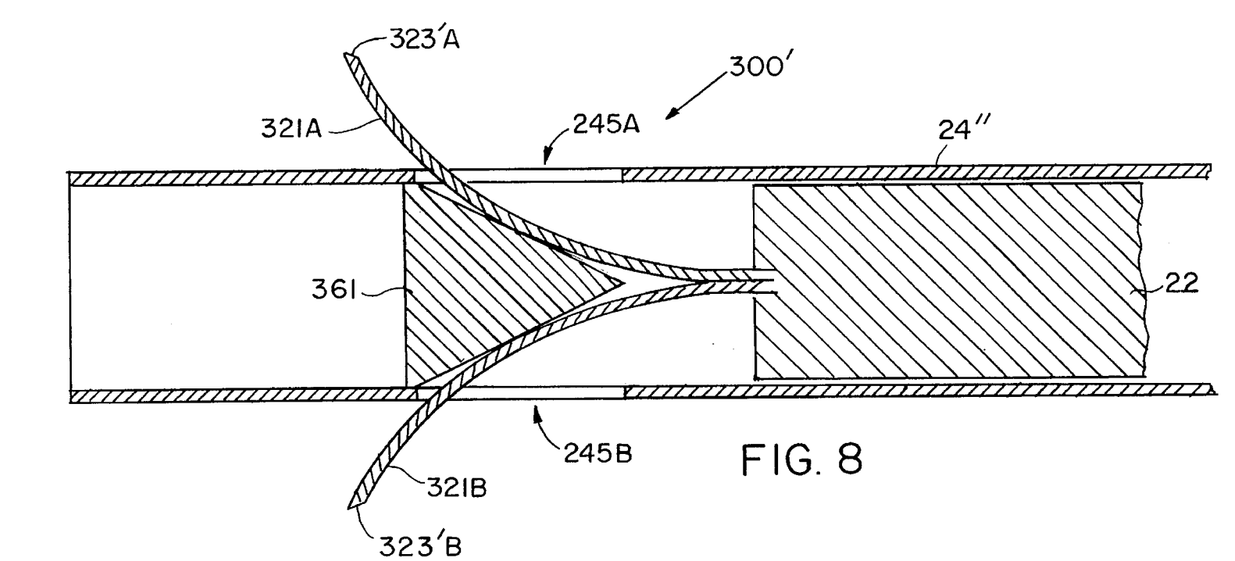
FIG. 8 is a cross sectional diagram of an alternate cutting assembly with a flexible cutting blade.

FIG. 8 is a cross sectional diagram of an alternative cutting assembly 300' with a flexible metal cutting blade. As illustrated, the cutting blade has two opposing halves 321A, 321B, each with a respective blade edge 323'A, 323'B. As the drive shaft 22 is urged forward, a deflection wedge or cam 361 separates the opposing cutting blades 321A, 321B and radially projects them through respective openings 245A, 245B in a torque tube 24". Although two blades are illustrated, there may be only a single blade or there may be more than two cutting blades. The deflection wedge 361 is shaped to separate and deflect the blades radially outwardly from the torque tube 24".

Figure 9:
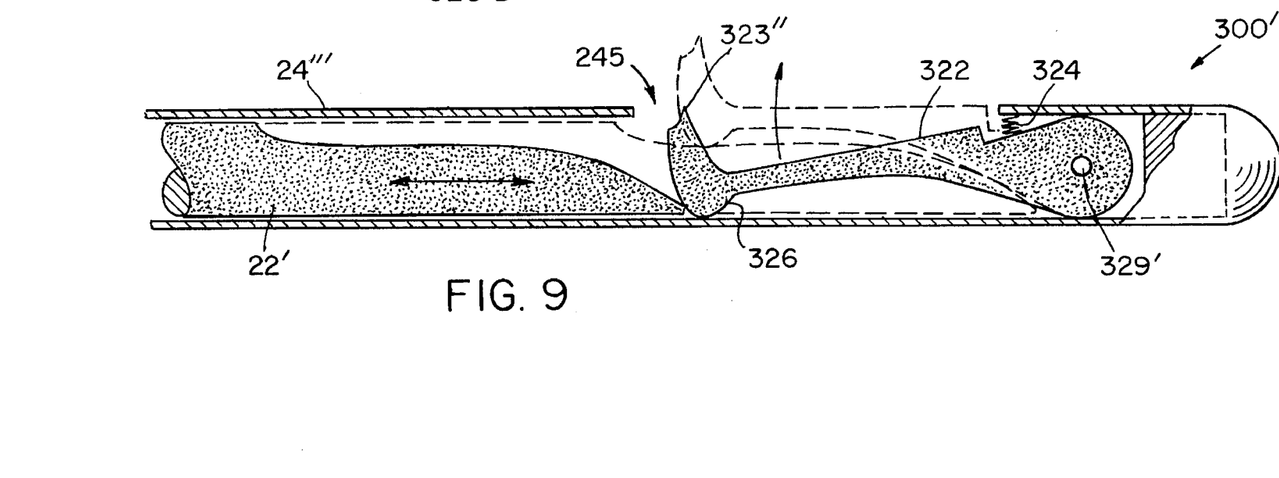
FIG. 9 is a cross sectional diagram of another alternate cutting assembly with a hammer cutting blade.

FIG. 9 is a cross sectional diagram of another alternative cutting assembly 300" with a hammer cutting blade. As illustrated, the drive shaft is a linear cam 22' disposed within the torque tube 24'". A hammer blade is fastened to the torque tube 24'" by a pivot joint 329'. The hammer blade includes cutting blade tip 323" on a head 326, which is connected to the pivot joint 329' by an arm 322. As the linear cam 22' is urged toward the distal end of the torque tube 24'", the blade tip 323" is urged out of a void 245 in the torque tube 24'" as shown in phantom. A spring 324 is biased to return the blade tip 323 to the rest position within the torque tube 24'" when the linear cam 22' is disengaged from the blade head 326. As illustrated, only one hammer blade is illustrated, but more than one blade can be employed. For example, a two-sided linear cam can be used to operate a pair of blade heads 326.

Figure 10:
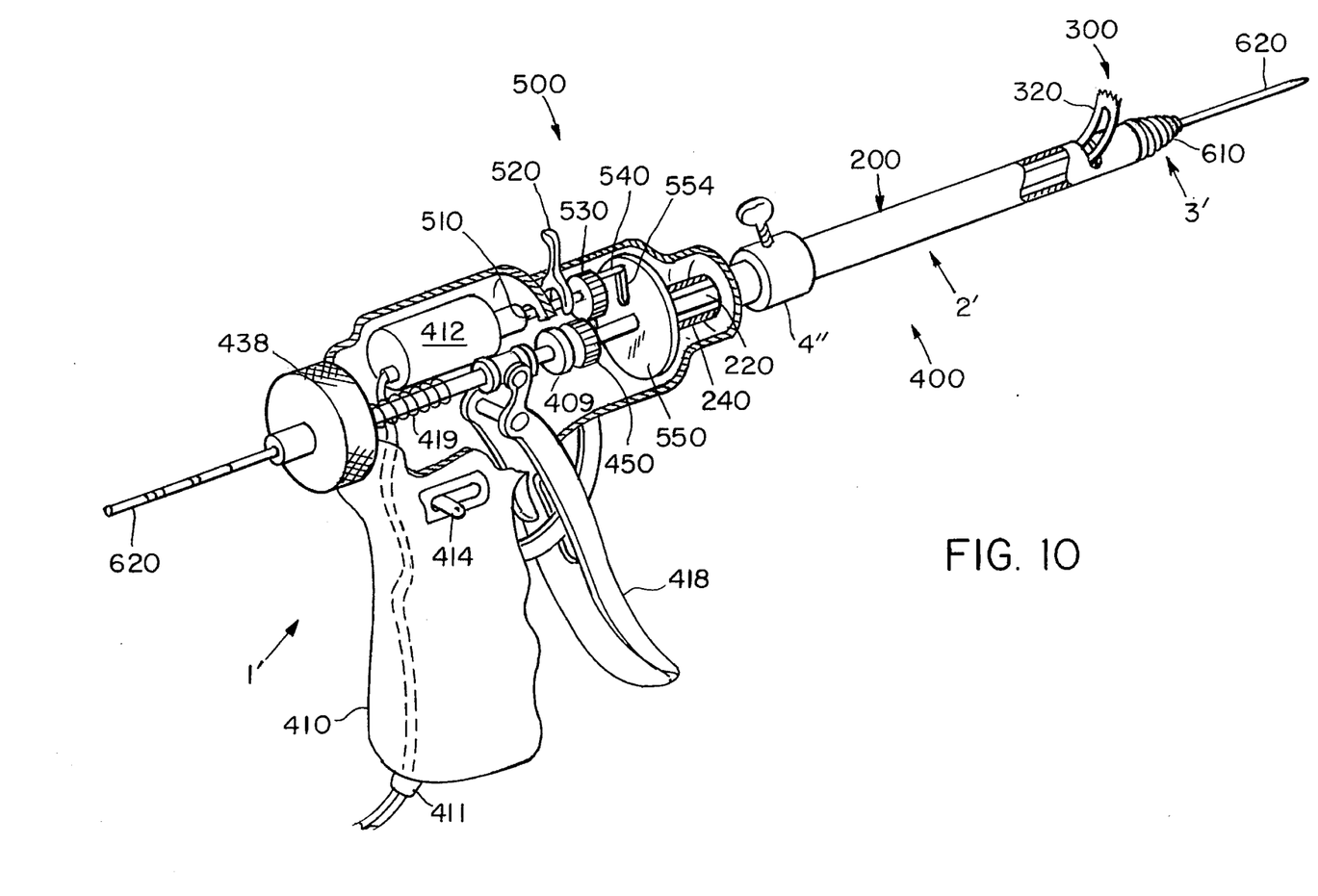
FIG. 10 is a perspective view of another embodiment of a bone saw according to the invention with portions of the housing broken away.

FIG. 10 is a perspective view of another embodiment of an intramedullary surgical tool 400 according to the invention with portions of the housing 410 broken away. The surgical tool comprises a drive body 1', a shaft 2' and a surgical head 3'. As previously described, the shaft 2' can be either a rigid member for use with a particular bone or a flexible member for use with different bones. A depth stop 4" clamps over the shaft 2' at a predetermined distance from the surgical head 3'.

The surgical tool 400 operates similarly to the bone cutting saw of FIG. 1, except the surgical tool 400 preferably includes an oscillating cutting assembly 300 and an integral reamer tip 610. During use, the shaft 2' and a surgical head 3' are inserted into a bored intramedullary canal of a bone, similar to that shown in FIG. 7.

The body 1' comprises a housing 410, a blade advancement handle 418 and a slide rheostat speed control 414. A fail safe return spring 419 is biased to place the cutting blade 320 in a steady state position (i.e., within the shaft 2').

The shaft 200 includes an internal drive shaft 220 in an outer tube 240. The drive shaft 220 is suspended within the housing 410 by at least one bearing 409. The drive shaft 220 and the outer tube 240 operate similarly to the aforementioned drive shaft 22 and outer tube 24 of FIG. 1. However, as illustrated the drive shaft 220 is cannulated to accept a central guide wire 620 through its entire length. Although not illustrated, a saline irrigation nozzle can supply irrigating saline solution into the outer tube 240 to rinse and cool the bone tissue during the surgery. Also not shown is an outer sheath such as the sheath 28 of FIG. 4, which is preferably included on the surgical tool 400.

As also illustrated, the shaft 200 includes a cannulated reamer tip 610 at the distal end of the shaft 200. The central guide wire 620 extends through the cannulated drive shaft 220 and out the cannulated reamer tip 610. During reaming operations, the cutting blade 320 is retracted into the shaft 200. The cutting blade 320 is extended beyond the shaft 200 only for bone cutting. An adjustment knob 438 coupled to the proximal end of the drive shaft 220 is used by the surgeon to limit the cutting diameter of the cutting assembly 300. After the bone is reamed and cut, a guide wire 620 can be inserted through the drive shaft 220 and the reamer tip 610. The surgical tool 400 is then removed, leaving the guide wire 620 within the bored intramedullary canal. The guide wire 620 can then be used to guide other tools through the bone fragments of a reduced fracture.

Figure 11A:
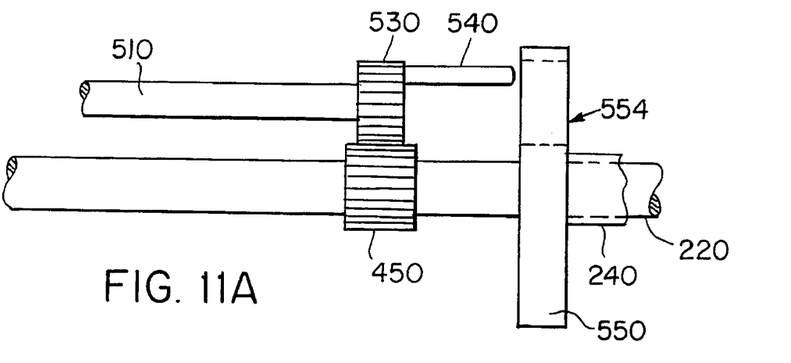
FIGS. 11A–11B are schematic diagrams of the gears of FIG. 10 operating in the rotary mode and oscillation mode, respectively.
Figure 11B:
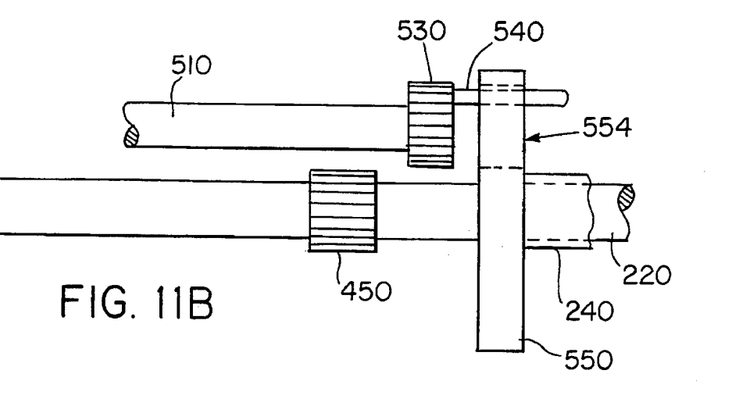

FIGS. 11A–11B are schematic diagrams of the gears 450, 530 of FIG. 10 operating in the rotary mode and oscillation mode, respectively. A select arm 520 is provided so the surgeon can select between the oscillation and rotation modes. More specifically, the select arm 520 is coupled to a spline-type drive shaft 510 by a collar (not shown) to translate the driving gear 530 and crank member 540 longitudinally relative to the drive shaft 510.

As illustrated in FIG. 11A, the motor gear 530 is meshed with the shaft drive gear 450. The crank member 540 is not engaged with the rocker disk 550. Note that the crank member 540 cannot engage the rocker disk 550 while the motor drive gear 530 is engaged with the shaft drive gear 450.

As illustrated in FIG. 11B, the motor gear 530 no longer engages the shaft drive gear 450. The crank member 540 is engaged with the aperture 554 of the rocker disk 550. The surgeon preferably aligns the aperture 554 with the crank member 540 by manually gripping and rotating the torque tube 240 until the aperture 554 receives the crank member 540. It being understood that the alignment can be done mechanically in automatic response to the select arm 520. As the motor gear 530 rotates, the crank member 540 causes the rocker disk 550 to oscillate, which in turn oscillates the torque tube 240 and the cutting assembly 300. The oscillating cutting assembly 300 cuts bone but will not cut soft tissue. The surgeon can adjust the oscillation frequency using the rheostat speed control 414. The frequency range can be selected by choosing the gear ratio between the motor gear 530 and the shaft drive gear 450 and the size of the aperture 554.

Returning to FIG. 10, a variable speed motor 412 within the drive body 1' is coupled to a power source (not shown) by a coupling 411. The motor 412 drives the drive shaft 220 in one of two modes selected by the surgeon. In a rotation mode, a motor gear 530 coupled by a drive shaft 510 to the motor 412 meshes with a drive shaft gear 450. Rotation of the motor gear 530 causes a corresponding rotation of the drive shaft gear 450. In an oscillation mode, an eccentric crank member 540 on the motor gear 530 meshes with a rocker disk 550. In particular the crank member 540 is inserted into a elongated aperture 554 in the rocker disk 550.

Figure 12:
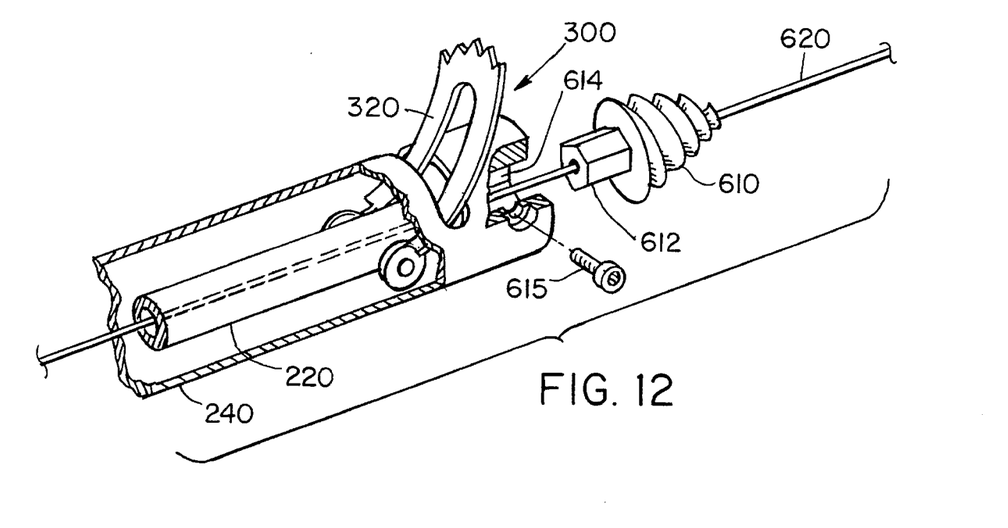
FIG. 12 is a foreshortened perspective view of a reamer tip of the bone saw of FIG. 10 with portions of the torque tube broken away.

FIG. 12 is a perspective view of the reamer of FIG. 10 with portions of the torque tube 240 and drive shaft 220 broken away. The reamer tip 610 includes a male hex coupling 612, which mates with a female hex coupling 614 of the torque tube 240. A set screw 615 clamps the reamer tip 610 to the torque tube 240. Preferably, the set screw 615 is flush with the torque tube 240.

Equivalents

Those skilled in the art will know, or be able to ascertain using no more than routine experimentation, many equivalents to the specific embodiments of the invention described herein. These and all other equivalents are intended to be encompassed by the following claims.

The invention claimed is:

1. A saw for cutting a bone having an intramedullary canal comprising:

a tube having a longitudinal axis and a side wall with a slot therethrough, the tube positionable within the intramedullary canal of the bone;

a cutting blade movable transversely of the longitudinal axis of the tube and through the slot between a rest location within the tube and a working location outside the tube and within the bone;

an actuating mechanism coupled to the cutting blade for moving the cutting blade through the slot, alternately between the rest location and the working location; and a motor coupled to the cutting blade to operate the cutting blade about the longitudinal axis of the tube to cut the bone when the cutting blade is in the working location.

2. The saw of claim 1 wherein the cutting blade is extendable from the rest location within the tube to the working location.

3. The saw of claim 2 further comprising an actuator coupled to the actuating mechanism.

4. The saw of claim 1 wherein the motor is selected from the group consisting of a hydraulic motor, an electric motor and an air motor.

5. The saw of claim 1 wherein the actuating mechanism is a shaft coupled to the motor and the cutting blade such that the motor transfers torque to the cutting blade through the shaft.

6. The saw of claim 1 wherein the tube is rigid.

7. The saw of claim 1 wherein the tube is flexible.

8. The saw of claim 5 where the shaft is cannulated.

9. The saw of claim 1 further comprising a reamer coupled to the motor for boring the intramedullary canal.

10. The saw of claim 1 wherein the reamer is cannulated.

11. The saw of claim 1 further comprising an oscillator to oscillate the cutting blade.

12. An intramedullary saw for cutting a bone having an intramedullary canal comprising:

an elongate tubular member disposable longitudinally within the intramedullary canal, the tubular member having a longitudinal axis and a side wall with a slot therethrough;

a cutting blade responsive to the tubular member and extendable transversely of the longitudinal axis of the tubular member and through the slot between a rest position within the tubular member and a working position outside the tubular member;

an elongate actuating member disposed within the tubular member and in communication with the cutting blade, longitudinal displacement of the actuating member displacing the cutting blade, alternately between the rest position and the working position;

an activator coupled to the actuating member to displace the actuating member in response to actions of a user; and a motor coupled to the tubular member to operate the cutting blade about the longitudinal axis of the tubular member by operating the tubular member to cut the bone when the cutting blade is in the working position.

13. The saw of claim 12 wherein the activator is a handgrip.

14. The saw of claim 12 wherein the motor is selected from the group consisting of a hydraulic motor, an electric motor and an air motor.

15. The saw of claim 12 wherein the cutting blade is coupled to the actuating member by a pivot.

16. The saw of claim 12 wherein the blade is coupled to the tubular member and the actuating member is a cam, the cam operating on the blade to extend the blade.

17. The saw of claim 12 wherein the blade is a flexible blade having a memory for the rest position.

18. The saw of claim 12 wherein the actuating member and the tubular member are rigid.

19. The saw of claim 12 wherein the actuating member and the tubular member are flexible.

20. The saw of claim 12 wherein the actuating member is cannulated.

21. The saw of claim 12 wherein the working position is variable and selected by the activator.

22. The saw of claim 12 wherein the motor is a variable speed motor, the motor speed being varied in response to actions of the user.

23. The saw of claim 12 further comprising a reamer coupled to the motor, the motor rotating the reamer to bore the intramedullary canal.

24. The saw of claim 23 wherein the reamer is coupled to the motor by the tubular member.

25. The saw of claim 23 wherein the reamer is cannulated.

26. The saw of claim 12 wherein the cutting blade is operated by rotation.

27. The saw of claim 12 wherein the cutting blade is operated by oscillation.

28. A method for cutting a bone having an intramedullary canal, comprising the steps of:

providing a tube having a longitudinal axis and a side wall with a slot therethrough;

positioning a cutting blade in a rest location within the tube;

positioning the tube within the intramedullary canal of the bone;

coupling the cutting blade to a motor and an actuating mechanism for moving the cutting blade through the slot;

disposing the cutting blade transversely of the longitudinal axis of the tube and through the slot from the rest location to a working location outside the tube and within the bone; and operating the cutting blade about the longitudinal axis of the tube with the motor to cut the bone when the cutting blade is in the working position.

29. The method of claim 28 wherein the step of disposing the cutting blade comprises extending the cutting blade from the rest location within the tube to the working location.

30. The method of claim 27 wherein the step of extending comprises varying the working position over time.

31. The method of claim 28 wherein the step of operating comprises oscillating the cutting blade.

32. The method of claim 28 wherein the step of operating comprises rotating the cutting blade by rotating the tube with the motor.

33. A saw for cutting a bone from within the intramedullary canal of the bone, the saw comprising:

a tube having a longitudinal axis and a side wall with a slot therethrough, the tube positionable within the bone;

a cutting blade positionable through the slot between a rest location within the tube and a working location outside the tube;

an actuator to urge the blade radially outwardly through the slot from the rest location toward the work location, transversely to the longitudinal axis of the tube; and a motor coupled to the blade to operate the blade about the longitudinal axis of the tube in the working location to cut the bone.

34. The saw of claim 33 wherein the actuator is manually operable.

35. The saw of claim 33 wherein the actuator is coupled to the blade.

36. The saw of claim 33 further comprising a linkage between the motor and the blade to rotate the blade.

37. The saw of claim 33 further comprising an oscillator to oscillate the blade.

38. An intramedullary surgical tool for operating within a bone having an intramedullary canal comprising:

a torque tube having a longitudinal axis and a side wall with a slot therethrough, the torque tube disposable longitudinally within the intramedullary canal;

a cutting blade extendable through the slot from a rest position within the torque tube to a working position outside the torque tube and transverse to the longitudinal axis of the torque tube;

an elongate actuating member disposed within the torque tube and in communication with the cutting blade, longitudinal displacement of the actuating member displacing the cutting blade from the rest position through the slot to the working position;

an activator coupled to the actuating member for displacing the actuating member in response to actions of a user; and a motor coupled to the torque tube to operate the cutting blade about the longitudinal axis of the torque tube to cut the bone when the cutting blade is in the working position by rotating the torque tube.

39. The surgical tool of claim 38 wherein the activator is a hand grip.

40. The surgical tool of claim 38 wherein the motor is selected from the group consisting of a hydraulic motor, an electric motor and an air motor.

41. The surgical tool of claim 38 wherein the cutting blade is coupled to the actuating member by a pivot.

42. The surgical tool of claim 38 wherein the blade is coupled to the torque tube and the actuating member is a cam, the cam registering to the blade to extend the blade.

43. The surgical tool of claim 38 wherein the blade is a flexible blade having a memory for the rest position.

44. The surgical tool of claim 38 wherein the actuating member and the torque tube are rigid.

45. The surgical tool of claim 38 wherein the actuating member and the torque tube are flexible.

46. The surgical tool of claim 38 wherein the actuating member is cannulated.

47. The surgical tool of claim 38 wherein the working position is a variable and selected by the activator.

48. The surgical tool of claim 38 wherein the motor is a variable speed motor, the motor speed being varied in response to actions of the user.

49. The surgical tool of claim 38 wherein the blade is operated by rotation.

50. The surgical tool of claim 38 wherein the blade is operated by oscillation.

51. In a motor-powered surgical tool disposable within an intramedullary canal of a bone, a cutting assembly for cutting the bone comprising:

a user control operable by a user;

a motor coupled to the user control;

a tube having a longitudinal axis and a side wall with a slot therethrough, the tube positionable within the bone; and a blade member having a cutting edge and coupled to the user control and the motor, the blade member responsive to an action of the user to incrementally extend the cutting edge from a rest position within the tube radially outwardly relative to the longitudinal axis of the tube to a working position through the slot and outside the tube, the cutting edge operable about the longitudinal axis of the tube by the motor to cut the bone when the blade member is in the working position.

52. The cutting assembly of claim 51 wherein the blade member comprises a plurality of blade members, each blade member having a respective cutting edge.

53. The cutting assembly of claim 51 wherein the blade member is flexible and has a memory for the rest position.

54. The cutting assembly of claim 53 wherein the blade member is a spring blade.

55. The cutting assembly of claim 51 wherein the blade member includes a pivot coupling the cutting edge to an elongate member.

56. The cutting assembly of claim 51 wherein the blade member is a hammer blade.

57. In a surgical tool disposable within an intramedullary canal of a bone, a cutting assembly for cutting the bone, comprising:

a user control operable by a user;

a tube having a longitudinal axis and a side wall with a slot therethrough, the tube positionable with the bone; and a blade member having a cutting edge, the blade member coupled to the user control and responsive to an action of the user to incrementally extend the cutting edge from a rest position within the tube radially outwardly relative to the longitudinal axis of the tube to a working position through the slot and outside the tube, the cutting edge operable about the longitudinal axis of the tube by the user to cut the bone when the blade member is in the working position, and wherein the blade member is flexible and has a memory for the rest position.

58. The cutting assembly of claim 57 wherein the blade member is a spring blade.

59. The cutting assembly of claim 57 wherein the blade member comprises a plurality of blade members.

60. The cutting assembly of claim 57 wherein the blade member is a hammer blade.

61. The surgical tool of claim 38 further comprising a reamer coupled to a distal end of the torque tube for boring the intramedullary canal by rotation of the torque tube by the motor.

62. The surgical tool of claim 61 wherein the reamer is cannulated.

63. The saw of claim 1 further comprising an irrigation conduit extending from a proximal end of the saw to a distal end of the saw adjacent to the cutting blade.

64. The saw of claim 12 further comprising an elongate irrigation conduit extending along the actuating member for delivering an irrigating fluid adjacent to the blade.

65. The method of claim 28 further comprising the step of delivering an irrigating fluid adjacent to the cutting blade through an irrigation conduit extending along the saw.

66. The saw of claim 33 further comprising an irrigation conduit extending lengthwise along the actuator to deliver an irrigating fluid adjacent to the blade.

67. The surgical tool of claim 38 further comprising an irrigation conduit disposed within the torque tube for delivering irrigating fluid adjacent to the cutting blade.

* * * * *